United States Patent
Beardsley et al.

(10) Patent No.: US 9,872,673 B2
(45) Date of Patent: Jan. 23, 2018

(54) SYSTEM AND METHOD FOR PERFORMING SURGICAL PROCEDURES WITH A REUSABLE INSTRUMENT MODULE

(71) Applicant: Covidien LP, Mansfield, MA (US)

(72) Inventors: John Beardsley, Wallingford, CT (US); Matthew Chowaniec, Middletown, CT (US); Russell Pribanic, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/990,164

(22) Filed: Jan. 7, 2016

(65) Prior Publication Data
US 2016/0113635 A1  Apr. 28, 2016

Related U.S. Application Data

(63) Continuation of application No. 13/719,377, filed on Dec. 19, 2012, now Pat. No. 9,241,757.
(Continued)

(51) Int. Cl.
*A61B 17/00* (2006.01)
*A61B 18/14* (2006.01)
(Continued)

(52) U.S. Cl.
CPC ........ *A61B 17/00* (2013.01); *A61B 17/07207* (2013.01); *A61B 18/14* (2013.01);
(Continued)

(58) Field of Classification Search
CPC . A61B 17/07207; A61B 18/14; A61B 19/081; A61B 2017/00115;
(Continued)

(56) References Cited

U.S. PATENT DOCUMENTS 4,091,880 A   5/1978  Troutner et al.
5,230,704 A   7/1993  Moberg et al.
(Continued)

FOREIGN PATENT DOCUMENTS

CN   102028509 A   4/2011
EP     0804124 B1   11/1997
(Continued)

OTHER PUBLICATIONS

Chinese Office Action (with English translation) dated Dec. 25, 2015, corresponding to Chinese Application No. 201310012945.0; 16 total pages.
(Continued)

*Primary Examiner* — Amanda Patton

(57) ABSTRACT

A surgical instrument includes an outer housing shell defining a cavity, the outer housing shell defining an upper outer housing half and a lower outer housing half, wherein the upper outer housing half defines a longitudinal axis and an instrument module selectively insertable into the cavity of the outer housing shell. The instrument module includes an inner housing shell, at least one motor disposed within the inner housing shell, a control board being in electrical communication with the at least one motor and an energy source being in electrical communication with the at least one motor and the control board. The instrument module is inserted into the cavity of the outer housing shell in such a manner that the operative axis of the at least one motor is substantially parallel to the longitudinal axis of the upper outer housing half.

20 Claims, 4 Drawing Sheets

Related U.S. Application Data

(60) Provisional application No. 61/586,201, filed on Jan. 13, 2012.

(51) Int. Cl.
*A61B 17/072* (2006.01)
*A61B 90/00* (2016.01)
*A61B 46/10* (2016.01)

(52) U.S. Cl.
CPC ..... *A61B 46/10* (2016.02); *A61B 2017/00115* (2013.01); *A61B 2017/00398* (2013.01); *A61B 2017/00464* (2013.01); *A61B 2017/00526* (2013.01); *A61B 2017/00734* (2013.01); *A61B 2017/00907* (2013.01); *A61B 2090/0813* (2016.02)

(58) Field of Classification Search
CPC  A61B 2017/00398; A61B 2017/00734; A61B 2017/00907; A61B 2019/4868
See application file for complete search history.

(56) References Cited

U.S. PATENT DOCUMENTS

| | | | |
|---|---|---|---|
| 5,499,992 | A | 3/1996 | Meade et al. |
| 5,746,759 | A | 5/1998 | Meade et al. |
| 5,752,972 | A | 5/1998 | Hoogeboom |
| 5,928,255 | A | 7/1999 | Meade et al. |
| 5,931,849 | A | 8/1999 | Desvignes et al. |
| 6,206,844 | B1 | 3/2001 | Reichel et al. |
| 7,468,041 | B2 | 12/2008 | Rhodes et al. |
| 8,221,449 | B2 | 7/2012 | Gadberry et al. |
| 8,894,647 | B2 | 11/2014 | Beardsley et al. |
| 9,155,529 | B2 | 10/2015 | Beardsley et al. |
| 2003/0149424 | A1 | 8/2003 | Barlev et al. |
| 2004/0116952 | A1 | 6/2004 | Sakurai et al. |
| 2006/0217729 | A1 | 9/2006 | Eskridge et al. |
| 2006/0226195 | A1 | 10/2006 | Scirica et al. |
| 2008/0077149 | A1 | 3/2008 | Hoegerle |
| 2010/0000074 | A1 | 1/2010 | Smith et al. |
| 2010/0057106 | A1 | 3/2010 | Sorrentino et al. |
| 2011/0017801 | A1 | 1/2011 | Zemlok et al. |
| 2011/0112517 | A1 | 5/2011 | Peine et al. |
| 2011/0125138 | A1* | 5/2011 | Malinouskas ........ A61B 17/068 606/1 |
| 2011/0306952 | A1 | 12/2011 | Chen et al. |
| 2012/0116266 | A1 | 5/2012 | Houser et al. |
| 2012/0238829 | A1 | 9/2012 | Shelton, IV et al. |
| 2012/0239010 | A1 | 9/2012 | Shelton, IV et al. |
| 2012/0253116 | A1 | 10/2012 | Sniffin et al. |
| 2012/0253328 | A1 | 10/2012 | Cunningham et al. |
| 2013/0184704 | A1 | 7/2013 | Beardsley et al. |
| 2013/0261643 | A1 | 10/2013 | Meade et al. |
| 2014/0207124 | A1 | 7/2014 | Aldridge et al. |
| 2016/0008080 | A1 | 1/2016 | Beardsley et al. |

FOREIGN PATENT DOCUMENTS

| | | |
|---|---|---|
| JP | H09538 | 1/1997 |
| JP | 2000254141 A | 9/2000 |
| JP | 2010051805 A | 3/2010 |
| JP | 2011078772 A | 4/2011 |
| WO | 2014/144780 A1 | 9/2014 |

OTHER PUBLICATIONS

European Search Report, dated Mar. 13, 2015, corresponding to European Application No. 13 15 1037.2; 7 pages.
Chinese First Office Action (with English translation), dated Jan. 26, 2016, corresponding to Chinese Application No. 201310013044.3; 16 total pages.
Chinese Second Office Action (with English translation), dated Aug. 4, 2016, corresponding to Chinese Application No. 201310012945.0; 18 total pages.
Japanese Office Action (with English translation), dated Aug. 30, 2016, corresponding to Japanese Application No. 2013-000854; 8 total pages.
Australian Patent Examination Report No. 1, dated Sep. 5, 2016, corresponding to Australian Application No. 2013200115; 3 pages.
Australian Patent Examination Report No. 1, dated Sep. 20, 2016, corresponding to Australian Application No. 2013200112; 3 pages.
European Search Report dated Feb. 8, 2017, corresponding to European Application No. 16179552.1; 11 pages.
European Search Report dated May 11, 2017, corresponding to European Application No. 16206726.8; 14 total pages.
European Search Report dated Oct. 4, 2017, corresponding to European Application No. 16206726.8; 19 total pages.

* cited by examiner

SYSTEM AND METHOD FOR PERFORMING SURGICAL PROCEDURES WITH A REUSABLE INSTRUMENT MODULE

CROSS REFERENCE TO RELATED APPLICATION

The present application is a Continuation Application claiming the benefit of and priority to U.S. patent application Ser. No. 13/719,377, filed on Dec. 19, 2012, which claims the benefit of and priority to U.S. Provisional Application Ser. No. 61/586,201, filed on Jan. 13, 2012, the entire contents of each of which are incorporated herein by reference.

The present application relates to U.S. patent application Ser. No. 13/719,344 (now U.S. Pat. No. 8,894,647), filed on Dec. 19, 2012, the entire contents of which are incorporated herein by reference.

BACKGROUND

Technical Field

The present disclosure relates generally to the field of reposable or reusable surgical instruments. In particular, the disclosure relates to instruments having separable and replaceable components to provide clean, sterile or refurbished surfaces in each instance of use.

Background of Related Art

One type of surgical device is a linear clamping, cutting and stapling device. Such a device may be employed in a surgical procedure to resect a cancerous or anomalous tissue from a gastro-intestinal tract. Conventional linear clamping, cutting and stapling instruments include a pistol grip-styled structure having an elongated shaft and distal portion. The distal portion includes a pair of scissors-styled gripping elements, which clamp the open ends of the colon closed. In this device, one of the two scissors-styled gripping elements, such as the anvil portion, moves or pivots relative to the overall structure, whereas the other gripping element remains fixed relative to the overall structure. The actuation of this scissoring device (the pivoting of the anvil portion) is controlled by a grip trigger maintained in the handle.

In addition to the scissoring device, the distal portion also includes a stapling mechanism. The fixed gripping element of the scissoring mechanism includes a staple cartridge receiving region and a mechanism for driving the staples up through the clamped end of the tissue against the anvil portion, thereby sealing the previously opened end. The scissoring elements may be integrally formed with the shaft or may be detachable such that various scissoring and stapling elements may be interchangeable.

A number of surgical device manufacturers have developed product lines with proprietary drive systems for operating and/or manipulating such surgical device. In many instances, such surgical device further includes a handle assembly, which is reusable, and a disposable end effector or the like that is selectively connected to the handle assembly prior to use and then disconnected from the end effector following use in order to be disposed of or in some instances sterilized for re-use.

Surgical devices that are reposable, or reusable for multiple procedures, reduce the instrumentation costs per procedure. Providing a reusable surgical device, however, presents various challenges. For example, the complexity of a surgical device tends to result in fairly labor intensive cleaning procedures to prepare the surgical device for subsequent use. Improper cleaning may result in dangerous contamination being introduced into the surgical site. Also, some reusable surgical devices have removable and replaceable components to provide clean surfaces for each use. Many of these surgical devices require arduous disassembly and reassembly procedures that require extensive training, and may discourage use of the surgical device.

SUMMARY

According to an embodiment of the present disclosure, a surgical instrument is provided. The surgical instrument includes an outer housing shell defining a cavity, the outer housing shell defining an upper outer housing half and a lower outer housing half, wherein the upper outer housing half defines a longitudinal axis and an instrument module selectively insertable into the cavity of the outer housing shell. The instrument module includes an inner housing shell, at least one motor disposed within the inner housing shell, the at least one motor including a drive shaft defining an operative axis of rotation, a control board disposed within the inner housing and being in electrical communication with the at least one motor and an energy source disposed within the inner housing and being in electrical communication with the at least one motor and the control board. The instrument module is inserted into the cavity of the outer housing shell in such a manner that the operative axis of the at least one motor is substantially parallel to the longitudinal axis of the upper outer housing half.

Additionally, the outer housing shell may be devoid of movable switches.

In an exemplary embodiment, the upper outer housing half and the lower outer housing half combine to form a pistol-grip configuration.

The outer housing shell may be at least partially translucent or at least partially transparent.

In another exemplary embodiment, the upper outer housing half includes at least one speaker for providing feedback information related to tissue parameters and surgical instrument parameters measured during a surgical procedure.

In yet another exemplary embodiment, the upper outer housing half includes at least one viewing window for viewing a display screen disposed therein displaying information related to tissue parameters and surgical instrument parameters measured during a surgical procedure. The display screen includes at least one of numerical indicators and color indicators.

Moreover, the control board electrically communicates with at least one processor for enabling flow of electrosurgical energy between the energy source and the at least one motor.

In yet another exemplary embodiment, the lower outer housing half includes an instrument shell cover hingedly connected thereto, the instrument shell cover configured to swivel into place after the instrument module is inserted into the cavity of the outer housing shell. Alternatively, an instrument shell cover is attached to at least a portion of the lower outer housing half, such that the upper and lower outer housing halves attach to the instrument shell cover to form a secure connection.

The outer housing shell may define at least one opening formed in a distal surface thereof for receiving the drive shaft therethrough when the instrument module is fully disposed in the outer housing shell.

A seal may be supported in the opening formed in the distal surface of the outer housing shell, wherein the seal forms a fluid-tight seal between the outer housing shell and the drive shaft.

The instrument module may include a plurality of motors each including a drive shaft extending therefrom. The outer housing shell may define a plurality of openings formed in a distal surface thereof for receiving a respective drive shaft therethrough when the instrument module is fully disposed in the outer housing shell. A seal may be supported in each opening formed in the distal surface of the outer housing shell, wherein each seal forms a fluid-tight seal between the outer housing shell and the respective drive shaft.

In another exemplary embodiment, a method of performing a surgical procedure is presented. The method includes the steps of providing an outer housing shell defining a cavity, the outer housing shell defining an upper outer housing half and a lower outer housing half, wherein the upper outer housing half defines a longitudinal axis and selectively inserting an instrument module into the cavity of the outer housing shell. The instrument module includes an inner housing shell, at least one motor disposed within the inner housing shell, the at least one motor including a drive shaft defining an operative axis of rotation, a control board disposed within the inner housing and being in electrical communication with the at least one motor and an energy source disposed within the inner housing and being in electrical communication with the at least one motor and the control board. The instrument module is inserted into the cavity of the outer housing shell in such a manner that the operative axis of the at least one motor is substantially parallel to the longitudinal axis of the upper outer housing half.

The outer housing shell may be at least partially translucent or at least partially transparent.

The outer housing shell may define at least one opening formed in a distal surface thereof for receiving the drive shaft therethrough when the instrument module is fully disposed in the outer housing shell.

A seal may be supported in the opening formed in the distal surface of the outer housing shell, wherein the seal forms a fluid-tight seal between the outer housing shell and the drive shaft.

The instrument module may include a plurality of motors each including a drive shaft extending therefrom. The outer housing shell may define a plurality of openings formed in a distal surface thereof for receiving a respective drive shaft therethrough when the instrument module is fully disposed in the outer housing shell. A seal may be supported in each opening formed in the distal surface of the outer housing shell, wherein each seal forms a fluid-tight seal between the outer housing shell and the respective drive shaft.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figures 1A, 1B:
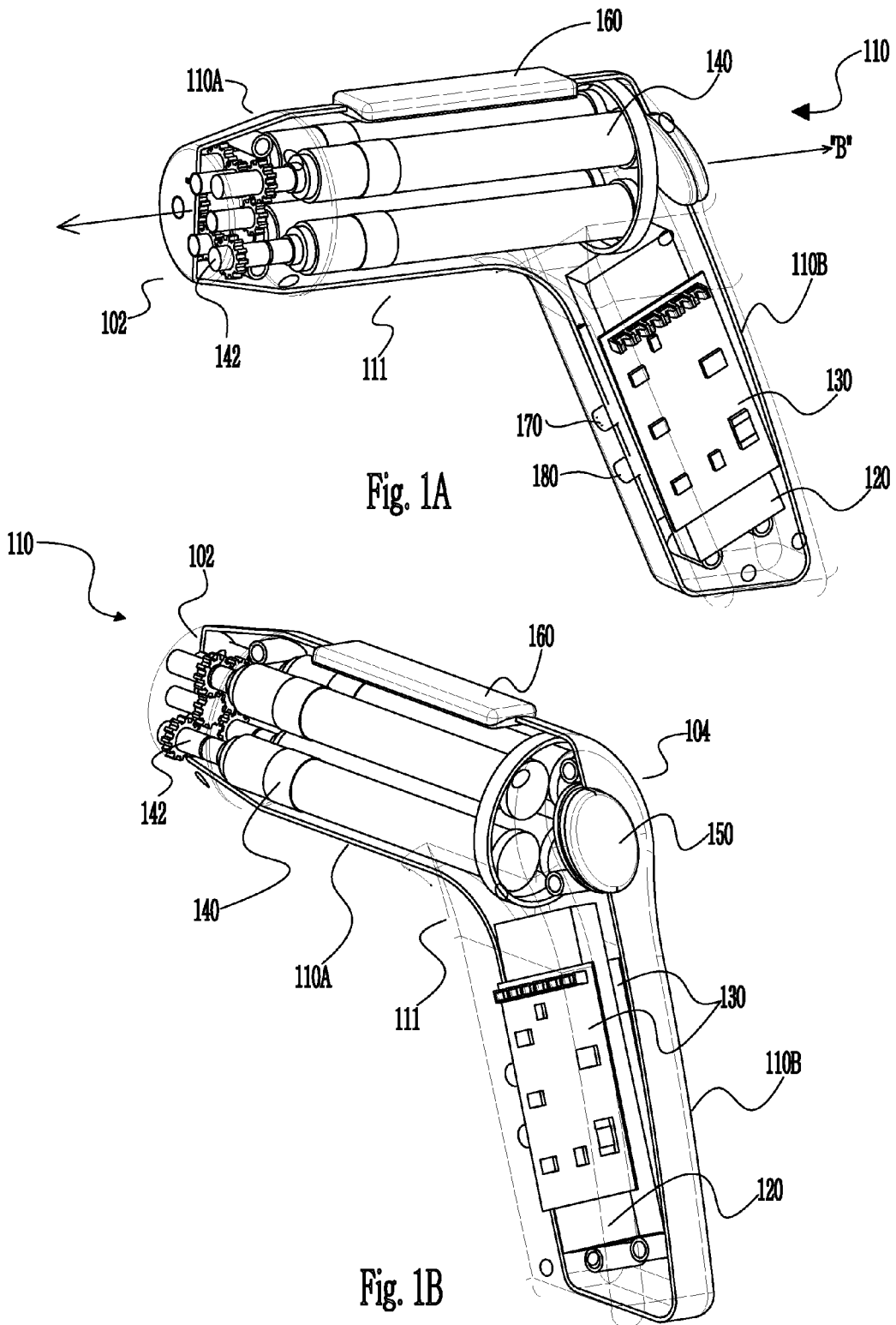
FIGS. 1A and 1B illustrate perspective views of a reusable surgical instrument module, in accordance with the present disclosure.

Embodiments of the presently disclosed apparatus will now be described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user.

Referring to FIGS. 1A and 1B, perspective views of a reusable surgical instrument module 110 are illustrated, in accordance with the present disclosure.

Instrument module 110 defines an upper instrument module half 110A and a lower instrument module half 110B, upper instrument module half 110A defining a longitudinal axis "B." Instrument module 110 also includes an inner housing shell 111 for incorporating a plurality of components therein, as described below.

Upper instrument module half 110A includes at least one motor 140, as well as a display screen 160. At least one motor 140 is disposed within inner housing shell 111. A distal end 102 of upper instrument module half 110A is configured to receive an end effector assembly (not shown). End effector assembly may be at least one of jaw members, a clip applier, vessel sealing devices, circular stapling devices, dissectors, retractors, cutters, graspers, and drills.

Lower instrument module half 110B includes a battery 120 (or energy source) and at least one control board 130. Battery 120 and at least one control board 130 are disposed within inner housing shell 111. Lower instrument module half 110B is configured to be gripped by a user, such as surgeon, during a surgical procedure. Additionally, upper instrument module half 110A and lower instrument module half 110B may combine to form a substantially L-shaped or pistol-grip configuration.

At least one control board 130 is connected, on the one hand, electrically to battery 120, and, on the other hand, to at least one motor 140. To this end, electric contacts (not shown) are provided on an upper side of battery 120 for establishing an electric connection with at least one control board 130. Additionally, at least one control board 130 electrically communicates with at least one processor (not shown) for enabling flow of electrosurgical energy between the energy source (e.g., battery 120) and each motor 140.

Each motor 140 is configured to include, for instance, a drive shaft 142. Drive shaft 142 defines an operative axis of rotation "B." Each motor 140 is configured to actuate a function or operation of an end effector assembly (not shown), including but not limited to, articulating, rotating, closing of the jaw members, ejecting fasteners, cutting, and the like.

Instrument module 110 may include a speaker 150 (see FIG. 1B), at a proximal end 104 thereof, for providing feedback information related to tissue parameters and surgical instrument parameters measured during a surgical procedure. Speaker 150 may be used to provide audible feedback. Audible feedback may be used in conjunction with or in lieu of the visual outputs.

Instrument module 110 may include display screen 160 disposed therein displaying information related to tissue parameters and surgical instrument parameters measured during a surgical procedure. Display screen 160 may be configured to provide the surgeon with a variety of suitable output information. Display screen 160 may include at least one of numerical indicators and color indicators.

Instrument module 110 may also include a clamp button 170 and a return button 180. Clamp button 170 may be configured to actuate an end effector assembly (not shown) connected to distal end 102 of instrument module 110 to a first position. End effector assembly may be a pair of jaw members for clamping tissue in the first position. Return button 180 may be configured to return the jaw members to an open, unclamped position (or second position).

Figure 2:
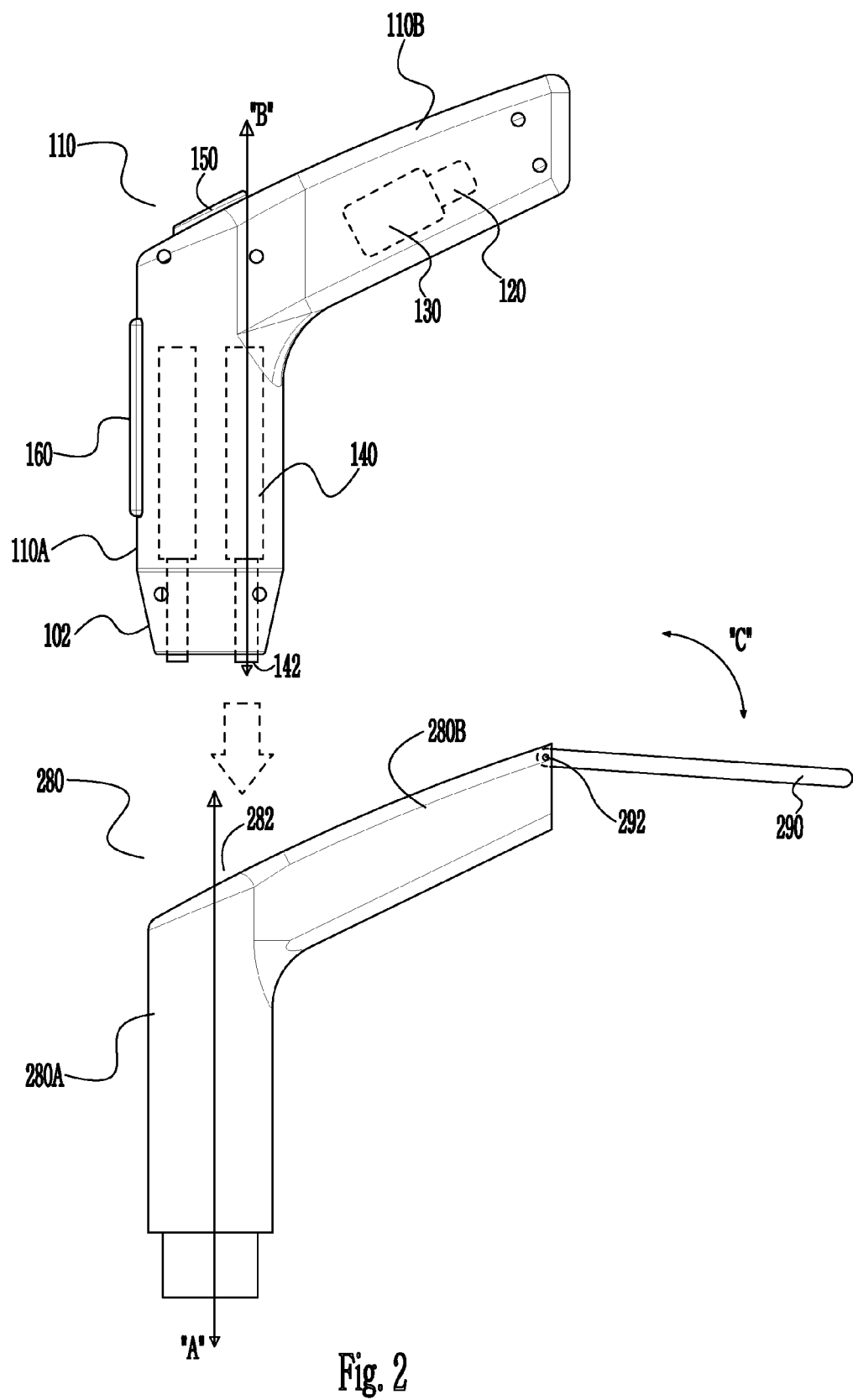
FIG. 2 illustrates a reusable surgical instrument module inserted into an outer housing shell having a hinged instrument cover shell, in accordance with an embodiment of the present disclosure.

Referring to FIG. 2, a method of inserting a reusable surgical instrument module 110 into an outer housing shell 280 having a hinged instrument cover shell 290, in accordance with an embodiment of the present disclosure is presented.

Outer housing shell 280 defines a cavity 282 therein. Outer housing shell 280 defines an upper outer housing half 280A and a lower outer housing half 280B. Upper outer housing half 280A defines a longitudinal axis "A" extending therethrough. Outer housing shell 280 also includes instrument shell cover 290 connected to lower outer housing half 280B via a hinged connection 292. Instrument shell cover 290 may rotate or pivot in direction "C" after instrument module 110 has been fully inserted into outer housing shell 280, as described below. In accordance with an embodiment of the present disclosure, outer housing shell 280 may be devoid of movable switches.

In operation or use, instrument module 110 is inserted into cavity 282 of outer housing shell 280 in such a manner that operative axis "B" of at least one motor 140 is substantially parallel to longitudinal axis "A" of upper outer housing half 280A. Stated differently, instrument module 110 is configured to be inserted into reusable outer housing shell 280, such that instrument module 110 is inserted and extracted along an axis of operation of at least one motor 140 or along longitudinal axis "B." Upper instrument module half 110A is configured to underlie or nest upper outer housing half 280A, whereas lower instrument module half 110B is configured to underlie or nest lower outer housing half 280B. Once instrument shell 110 is fully inserted into outer housing shell 280, instrument shell cover 290 is rotated, in direction "C," in order to create a secure seal with outer housing shell 280.

Following a surgical procedure, instrument shell cover 290 is opened and instrument module 110 is withdrawn from or removed from cavity 282 of outer housing shell 280 such that outer housing shell 280 and shell cover 290 may be cleaned in accordance with methods and procedures known in the art, for example, sterilizing, autoclaving, steam cleaning, wiping with cleaning products/solvents and the like. Thus, outer housing shell 280 and shell cover 290 may be cleaned or sterilized without compromising instrument module 110 inserted therein. Once cleaning or sterilization has been completed, instrument module 110 may be re-introduced into cavity 282 of outer housing shell 280 prior to performing a further surgical procedure.

Figure 3:
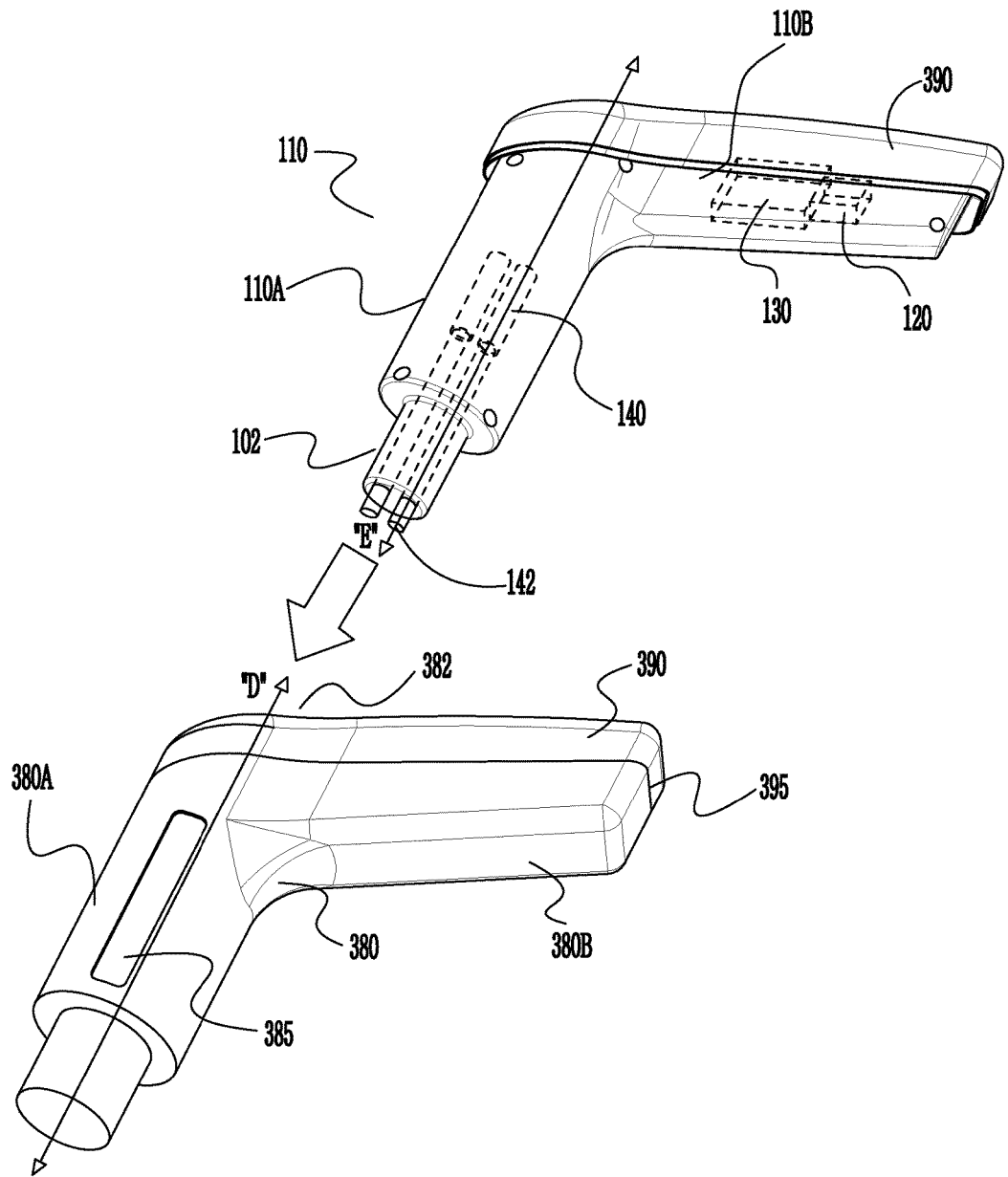
FIG. 3 illustrates a reusable surgical instrument module inserted into an outer housing shell having a snapable instrument cover shell, in accordance with another embodiment of the present disclosure.

Referring to FIG. 3, a method of inserting a reusable surgical instrument module 110 into an outer housing shell 380 having a snapable instrument cover shell 390, in accordance with another embodiment of the present disclosure is illustrated.

Outer housing shell 380 defines a cavity 382 therein. Outer housing shell 380 defines an upper outer housing half 380A and a lower outer housing half 380B. Upper outer housing half 380A defines a longitudinal axis "D" extending therethrough. Lower outer housing half 380B of outer housing shell 380 may connect or attach to instrument shell cover 390 via, for example, a snapable mechanism including fasteners (not shown). Additionally, a clear viewing window 385 may be constructed so that it overlays a display screen (e.g., as described above with reference to FIGS. 1A and 1B). Viewing window 385 is designed for viewing the display screen disposed therein displaying information related to tissue parameters and surgical instrument parameters measured during a surgical procedure.

In accordance with the present disclosure, it is contemplated that outer housing shell 380 (as well as outer housing shells 180, 280) may be fabricated from a translucent or transparent material, such as, for example, a polycarbonate resin thermoplastic. As so constructed, indicia from display screen 160 of instrument module 110 or the like. It is further contemplated that at least a portion of outer housing shell 380 may be translucent or transparent.

In operation or use, instrument module 110 is inserted into cavity 382 of outer housing shell 380 in such a manner that operative axis "E" of at least one motor 140 (or of at least one drive shaft 142) is substantially parallel to longitudinal axis "D" of upper outer housing half 110A. Stated differently, instrument module 110 is configured to be inserted into instrument outer housing shell 380, such that instrument module 110 is inserted and extracted along an axis of operation of at least one motor 140, or along longitudinal axis "E." Upper instrument module half 110A is configured to underlie or nest upper outer housing half 380A, whereas lower instrument module half 110B is configured to underlie or nest lower outer housing half 380B. Once instrument shell cover 390 is attached to a portion of lower outer housing half 380B, instrument module 110 is inserted into outer housing shell 380 such that upper outer housing half 380A and the remaining portion of the lower outer housing half 380B lock or secure or seal with instrument shell cover 390 along connection region 395.

Following a surgical procedure, instrument shell cover 390 is withdrawn or unsnapped from lower outer housing half 380B (at connection region 395) and instrument module 110 is withdrawn from or removed from cavity 382 of outer housing shell 380 such that outer housing shell 380 and shell cover 390 may be cleaned in accordance with methods and procedures known in the art. Thus, outer housing shell 380 may be cleaned or sterilized without compromising instrument module 110 inserted therein. Once cleaning or sterilization has been completed, instrument module 110 may be re-introduced into cavity 382 of outer housing shell 380 prior to performing a further surgical procedure.

Figure 4:
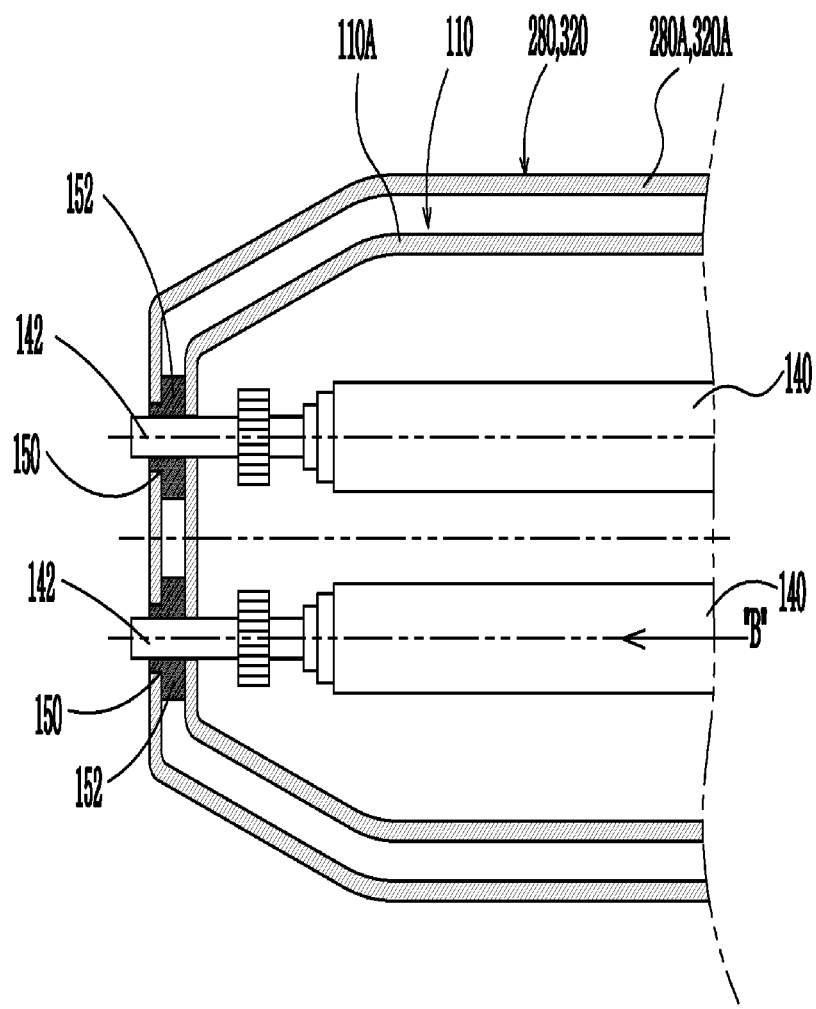
FIG. 4 is an enlarged, schematic, longitudinal cross-sectional view illustrating the reusable surgical instrument module inserted into the outer housing shell, and showing seals disposed about drive shafts of the reusable surgical instrument module.

Turning now to FIG. 4, in accordance with the present disclosure, it is contemplated that outer housing shell 280, 380 may define a plurality of apertures 150 through which each drive shaft 142 passes. A seal 152 is provided in each aperture 150 and is supported therein so as to remain with outer housing shell 280, 380 during insertion/retraction of instrument module 110 therein/therefrom. Seals 152 may take the form of O-rings or the like, and may be constructed from a resilient, polymeric material, such as, for example, rubber. Seals 152 are configured and dimensioned to establish a fluid-tight seal between outer housing shell 280, 380 and drive shafts 142. Additionally, seals 152 are configured and dimensioned to permit drive shafts 142 to rotate. In use, when shell covers 290, 390 are closed against respective outer housing shells 280, 380, a force is exerted against instrument module 110, substantially along or in direction "B", to thereby press a distal surface of upper instrument module half 110A against seals 152 and establish a fluid-tight seal against an outer surface of drive shafts 142.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

What is claimed is:

1. A method of assembling a surgical instrument, the method comprising:
   providing an outer housing shell that defines a cavity, the outer housing shell including an upper outer housing and a lower outer housing extending from the upper outer housing, the outer housing shell having a face that defines an opening that is in communication with the cavity;
   providing an instrument module including an inner housing shell that defines a cavity therein, the inner housing shell having an upper inner housing and a lower inner housing extending from the upper inner housing; and
   inserting the instrument module into the cavity of the outer housing shell through the opening of the outer housing shell, thereby positioning the upper inner housing of the inner housing shell in the upper outer housing of the outer housing shell and the lower inner housing of the inner housing shell in the lower outer housing of the outer housing shell.

2. The method according to claim 1, wherein the instrument module passes through the upper outer housing and the lower outer housing when the instrument module is inserted into the cavity of the outer housing shell.

3. The method according to claim 1, wherein the instrument module is inserted into the cavity of the outer housing shell in such a manner that the operative axis of a motor of the instrument module is substantially parallel to a longitudinal axis defined by the upper outer housing.

4. The method according to claim 1, further comprising rotating an instrument shell cover relative to the lower outer housing after the instrument module is inserted into the cavity of the outer housing shell.

5. The method according to claim 1, further comprising passing a drive shaft of the instrument module through an opening formed in a distal surface of the outer housing shell.

6. The method according to claim 5, further comprising forming a fluid-tight seal between the outer housing shell, the inner housing shell, and the drive shaft.

7. The method according to claim 1, further comprising engaging an instrument shell cover with the face of the outer housing shell thereby covering the cavity and enclosing the inner housing shell of the instrument module within the cavity.

8. The method according to claim 1, further comprising sterilizing an outer surface of the outer housing shell.

9. A surgical instrument, comprising:
   an outer housing shell defining a cavity therein, the outer housing shell including:
   an upper outer housing; and
   a lower outer housing extending from the upper outer housing, the outer housing shell having a face defining an opening that is in communication with the cavity; and
   an instrument module including an inner housing shell that defines a cavity therein, the inner housing shell having an upper inner housing and a lower inner housing extending from the upper inner housing, wherein the instrument module is configured to be selectively received within the cavity of the outer housing shell through the opening of the outer housing shell such that the upper inner housing of the inner housing shell is positioned in the upper outer housing of the outer housing shell and the lower inner housing of the inner housing shell is positioned in the lower outer housing of the outer housing shell.

10. The surgical instrument according to claim 9, wherein the face of the outer housing shell is formed at a proximal end of the upper outer housing and a proximal end of the lower outer housing, the opening of the outer housing shell collectively defined by the upper outer housing and the lower outer housing.

11. The surgical instrument according to claim 9, wherein the instrument module includes a motor disposed in the cavity of the inner housing shell, the motor defining an operative axis that is substantially parallel to a longitudinal axis defined by the upper outer housing.

12. The surgical instrument according to claim 9, further comprising an instrument shell cover rotatably coupled to the lower outer housing and configured to selectively enclose the inner housing shell of the instrument module within the cavity of the outer housing shell.

13. The surgical instrument according to claim 9, wherein the instrument module further includes a drive shaft disposed in the cavity of the inner housing shell and configured to extend through an opening formed in a distal surface of the outer housing shell.

14. The surgical instrument according to claim 9, wherein the outer housing shell includes a seal supported in a distal portion thereof.

15. The surgical instrument according to claim 9, wherein the instrument module includes a circuit board disposed within the cavity of the inner housing shell.

16. A surgical instrument, comprising:
   an outer housing shell defining a cavity therein, the outer housing shell including:
   an upper outer housing; and
   a lower outer housing extending from the upper outer housing, the outer housing shell having a face defining an opening that is in communication with the cavity; and
   an instrument module including:
   an inner housing shell having an upper inner housing and a lower inner housing extending from the upper inner housing; and
   at least one of a motor disposed in the inner housing shell or a drive shaft disposed in the inner housing shell, wherein the instrument module is configured to be selectively received within the cavity of the outer housing shell through the opening of the outer housing shell such that the upper inner housing of the inner housing shell is positioned in the upper outer housing of the outer housing shell and the lower inner housing of the inner housing shell is positioned in the lower outer housing of the outer housing shell.

17. The surgical instrument according to claim 16, wherein the motor is disposed within the upper inner housing of the inner shell housing.

18. The surgical instrument according to claim 16, wherein the drive shaft is disposed within the upper inner housing of the inner shell housing.

19. The surgical instrument according to claim 16, wherein the motor defines an operative axis that is substantially parallel to a longitudinal axis defined by the upper outer housing.

20. The surgical instrument according to claim 16, wherein the drive shaft is configured to extend through an opening formed in a distal surface of the outer housing shell.

* * * * *